(12) United States Patent
Winterberg et al.

(10) Patent No.: US 9,371,255 B2
(45) Date of Patent: Jun. 21, 2016

(54) MIXED OXIDE COMPOSITIONS AND PROCESS FOR PREPARING ISOOLEFINS

(75) Inventors: Markus Winterberg, Datteln (DE); Christian Böing, Köln (DE); Dietrich Maschmeyer, Recklinghausen (DE); Asli Nau, Wetter (DE); Horst-Werner Zanthoff, Mülheim a.d. Ruhr (DE); Thomas Quandt, Marl (DE); Christian Schulze Isfort, Kapellen (BE)

(73) Assignee: Evonik Degussa GmbH, Essen (DE)

( * ) Notice: Subject to any disclaimer, the term of this patent is extended or adjusted under 35 U.S.C. 154(b) by 269 days.

(21) Appl. No.: 14/005,479

(22) PCT Filed: Mar. 7, 2012

(86) PCT No.: PCT/EP2012/053835
§ 371 (c)(1),
(2), (4) Date: Dec. 13, 2013

(87) PCT Pub. No.: WO2012/123292
PCT Pub. Date: Sep. 20, 2012

(65) Prior Publication Data
US 2014/0087940 A1 Mar. 27, 2014

(30) Foreign Application Priority Data
Mar. 16, 2011 (DE) .......................... 10 2011 005 608

(51) Int. Cl.
| C07C 1/22 | (2006.01) |
| B01J 21/12 | (2006.01) |
| C07C 1/213 | (2006.01) |
| B01J 37/10 | (2006.01) |
| B01J 37/28 | (2006.01) |
| B01J 23/00 | (2006.01) |
| B01J 23/04 | (2006.01) |
| B01J 27/16 | (2006.01) |
| B01J 27/18 | (2006.01) |
| B01J 35/00 | (2006.01) |
| B01J 35/10 | (2006.01) |
| C07C 29/00 | (2006.01) |

(52) U.S. Cl.
CPC . *C07C 1/22* (2013.01); *B01J 21/12* (2013.01); *B01J 23/002* (2013.01); *B01J 23/04* (2013.01); *B01J 27/16* (2013.01); *B01J 27/1806* (2013.01); *B01J 35/002* (2013.01); *B01J 35/0073* (2013.01); *B01J 35/1014* (2013.01); *B01J 35/1019* (2013.01); *B01J 37/10* (2013.01); *B01J 37/28* (2013.01); *C07C 1/213* (2013.01); *C07C 29/00* (2013.01); *B01J 2523/00* (2013.01); *C07C 2521/08* (2013.01); *C07C 2523/04* (2013.01); *C07C 2529/70* (2013.01); *Y02P 20/52* (2015.11); *Y02P 20/582* (2015.11)

(58) Field of Classification Search
CPC .......... C07C 1/22; C07C 29/00; C07C 1/213; C07C 2529/70; C07C 2523/04; C07C 2521/08; B01J 23/04; B01J 35/0073; B01J 23/002; B01J 35/002; B01J 35/1014; B01J 27/16; B01J 37/10; B01J 27/1806; B01J 37/28; B01J 35/1019; B01J 21/12; B01J 2523/00; Y02P 20/52
See application file for complete search history.

(56) References Cited

U.S. PATENT DOCUMENTS

| 5,227,564 | A | 7/1993 | Chen et al. |
| 6,328,944 | B1 * | 12/2001 | Mangold ................. A61K 8/25 423/278 |
| 6,657,090 | B2 | 12/2003 | Rix et al. |
| 6,881,700 | B2 | 4/2005 | Sakuth et al. |
| 7,354,883 | B2 | 4/2008 | Kaizik et al. |
| 7,361,714 | B2 | 4/2008 | Grass et al. |
| 7,473,812 | B2 | 1/2009 | Peters et al. |
| 7,723,261 | B2 | 5/2010 | Barth et al. |
| 7,737,318 | B2 | 6/2010 | Santiago-Fernandez et al. |
| 7,910,786 | B2 | 3/2011 | Winterberg et al. |
| 7,919,662 | B2 | 4/2011 | Winterberg et al. |
| 7,932,428 | B2 | 4/2011 | Rix et al. |
| 7,968,758 | B2 | 6/2011 | Winterberg et al. |
| 7,977,523 | B2 | 7/2011 | Zanthoff et al. |
| 8,269,050 | B2 | 9/2012 | Praefke et al. |
| 2003/0089279 | A1 | 5/2003 | Meyer et al. |
| 2006/0041167 | A1 | 2/2006 | Grass et al. |
| 2008/0058572 | A1 | 3/2008 | Fernandez et al. |
| 2009/0018366 | A1 | 1/2009 | Berweiler et al. |
| 2010/0144998 | A1 | 6/2010 | Santiago-Fernandez et al. |
| 2011/0060169 | A1 | 3/2011 | Kaizik et al. |
| 2011/0118523 | A1 | 5/2011 | Winterberg et al. |
| 2011/0152596 | A1 | 6/2011 | Zanthoff et al. |
| 2011/0217552 | A1 | 9/2011 | Schulze-Isfort et al. |
| 2012/0142985 | A1 | 6/2012 | Winterberg et al. |
| 2012/0149549 | A1 | 6/2012 | Boeing et al. |

FOREIGN PATENT DOCUMENTS

| CN | 101134169 A | 3/2008 |
| EP | 1 186 628 | 3/2002 |
| EP | 1 266 864 | 12/2002 |

OTHER PUBLICATIONS

U.S. Appl. No. 14/432,928, filed Apr. 1, 2015, Nau, et al.
Combined Taiwanese Office Action and Search Report issued Sep. 8, 2015 in Patent Application No. 101108464 (English Translation only).
Office Action issued Oct. 23, 2015 in Mexican Patent Application No. MX/a/2013/010519.
U.S. Appl. No. 13/997,677, filed Jun. 25, 2013, Schulze-Isfort, et al.
U.S. Appl. No. 13/880,862, filed Jul. 3, 2013, Winterberg, et al.
International Search Report Issued Aug. 6, 2012 in PCT/EP12/053835 Filed Mar. 7, 2012.
Japanese Office Action issued Aug. 3, 2015 in Patent Application No. 2013-558364 (English Translation only).

\* cited by examiner

*Primary Examiner* — Anthony J Zimmer
(74) *Attorney, Agent, or Firm* — Oblon, McClelland, Maier & Neustadt, L.L.P.

(57) ABSTRACT

The present invention relates to mixed oxide compositions, to the use thereof as a catalyst for cleavage of alkyl tert-alkyl ethers or tertiary alcohols, and to a process for cleaving alkyl tert-alkyl ethers or tertiary alcohols to isoolefins and alcohol or water.

7 Claims, No Drawings

MIXED OXIDE COMPOSITIONS AND PROCESS FOR PREPARING ISOOLEFINS

The present invention relates to mixed oxide compositions, to the use thereof as a catalyst for cleavage of alkyl tert-alkyl ethers or tertiary alcohols, and to a process for cleaving alkyl tert-alkyl ethers or tertiary alcohols to isoolefins and alcohol or water.

Isoolefins, for example isobutene, are important intermediates for the preparation of a multitude of organic compounds. Isobutene, for example, is a starting material for the preparation of butyl rubber, polyisobutylene, isobutene oligomers, branched $C_5$ aldehydes, $C_5$ carboxylic acids, $C_5$ alcohols and $C_5$ olefins. It is also used as an alkylating agent, especially for synthesis of tert-butyl aromatics, and as an intermediate for the production of peroxides. In addition, isobutene can be used as a precursor for methacrylic acid and esters thereof.

In industrial streams, isoolefins are usually present with other olefins and saturated hydrocarbons with the same number of carbon atoms. The isoolefins cannot be separated from these mixtures in an economically viable manner by physical separation methods alone.

For example, isobutene is present in customary industrial streams together with saturated and unsaturated $C_4$ hydrocarbons. Isobutene cannot be separated from these mixtures in an economically viable manner by distillation due to the small boiling point difference or the small separation factor between isobutene and 1-butene. Therefore, isobutene is frequently obtained from technical hydrocarbons by converting isobutene to a derivative which can be removed easily from the rest of the hydrocarbon mixture, and cleaving the isolated derivative back to isobutene and derivatizing agent.

Typically, isobutene is separated from $C_4$ cuts, for example the $C_4$ fraction from a steamcracker, as follows. After removing the majority of the polyunsaturated hydrocarbons, principally of the butadiene, by extraction/extractive distillation or selective hydrogenation to give linear butenes, the remaining mixture (raffinate I or selectively hydrogenated Crack $C_4$) is reacted with alcohol or water. Isobutene gives rise to methyl tert-butyl ether (MTBE), when methanol is used, to ethyl tert-butyl ether (ETBE) when ethanol is used, and to tert-butanol (TBA) when water is used. After they have been removed, these derivatives can be cleaved to isobutene in a reversal of their formation.

The cleavage of alkyl tert-butyl ethers (ATBEs) to the corresponding isoolefins and alcohols and the cleavage of tertiary alcohols to the corresponding isoolefins and water can be performed in the presence of acidic or basic catalysts in the liquid phase or gas/liquid mixed phase, or in the pure gas phase.

The literature describes a multitude of catalysts for the gas phase cleavage of alkyl tert-alkyl ethers (ATAEs) and tertiary alcohols to the corresponding isoolefins and alcohol or water. This is especially true of catalysts which are utilized for cleavage of methyl tert-butyl ether (MTBE).

The catalysts used are usually metal oxides with an empirical formula of $M_aO_x$, mixed metal oxide compositions with empirical formulae $M_aM_bM_nO_y$ where indices a, b, n, x, y may be whole or rational numbers, especially those which contain M=Si or M=Al, acids on metal oxide supports or metal salts.

U.S. Pat. No. 4,254,290 describes, as cleavage catalysts, for example, $SiO_2/Al_2O_3$ or $WO_3/Al_2O_3$. U.S. Pat. No. 4,320,232 and U.S. Pat. No. 4,521,638 claim, for cleavage of tertiary ethers, catalysts consisting of phosphoric acid on supports. Alumina on silica gel is used in U.S. Pat. No. 4,398,051 as a cleavage catalyst. For the same purpose, zeolites are used in the two patents U.S. Pat. No. 4,357,147 and U.S. Pat. No. 5,254,785.

JP 59010528 uses, as a cleavage catalyst, sulphated titanium dioxide or zirconium dioxide. For cleavage of ethers, U.S. Pat. No. 5,607,992 uses a zirconium oxide/cerium oxide catalyst, U.S. Pat. No. 6,124,232 zirconium oxide/tungsten oxide, and U.S. Pat. No. 6,162,757 a mixed oxide of zirconium and rare earths.

WO 2005-066101 claims a catalyst with the general empirical formula $X_mY_nZ_pO_q$ where X is at least one element of the fourth group of the periodic table of the elements, Y is at least one metal from the third and/or sixth group and Z is at least one element from the seventh, eighth or eleventh group.

JP 1993-229965 claims a catalyst with the empirical formula $Si_aX_bY_cZ_dO_e$. (Si and O here in each case represent silicon and oxygen; X is at least one element selected from the group consisting of titanium and zirconium; Y is an element selected from the group consisting of magnesium and calcium; Z is at least one element selected from the group consisting of sodium, potassium, chlorine and sulphur; a, b, c, d and e indicate the atomic ratio of the individual elements. When a=1, b=0.001 to 10, c=0.0001 to 5, d=0 to 1; e is the number of oxygen atoms necessary to satisfy the atomic valency of the aforementioned individual constituents).

U.S. Pat. No. 5,227,564 describes a gas phase process for preparing isoolefin by cleavage of the corresponding alkyl tert-alkyl ethers with the aid of a catalyst consisting of a mixture of a zeolitic material having a silicon to aluminium ratio of greater than 5 with an x-ray-amorphous oxide of the elements silicon, aluminium or a mixed oxide of the two elements.

U.S. Pat. No. 5,171,920 describes, inter alia, a mixed oxide of the elements silicon, aluminium and magnesium as a catalyst for ether cleavage. The preparation is accomplished by first impregnating silicon dioxide with an aqueous magnesium nitrate solution, an intermediate drying step and then a further impregnation with an aqueous aluminium nitrate solution. Subsequent preliminary drying is followed by calcining. The aluminium oxide content is 0.37% by mass (calculated as $Al_2O_3$) and the magnesium oxide content is 7.7% by mass (calculated as MgO).

EP 0 045 159 describes, inter alia, a mixed oxide of the elements silicon and aluminium with an aluminium oxide content of 13% by mass (calculated as $Al_2O_3$) as a catalyst for the cleavage of alkyl tert-alkyl ethers. The preparation is accomplished by grinding and then calcining a commercial precipitated silicon-aluminium mixed oxide with the corresponding ratio of the elements.

DE 292 486 9 describes a catalyst for the cleavage of alkyl tert-alkyl ethers based on crystalline silica which may be modified with metal oxides. One modification described is that with 0.2% by mass of aluminium oxide (calculated as $Al_2O_3$). The preparation is accomplished by precipitating, crystallizing and calcining tetraethyl orthosilicate in the presence of aluminium nitrate nonahydrate.

EP 0 589 557 describes, inter alia, a mixed oxide of the elements silicon, aluminium and magnesium as a catalyst for ether cleavage. In the preparation thereof, in a first step, a commercially available silicon-aluminium mixed oxide prepared by precipitation impregnated with an aqueous magnesium salt solution in such a way that, during the impregnation, the pH of the impregnation solution can be adjusted by addition of a base to a pH of 7 to 11. In order to obtain particularly active and selective catalysts, impregnation times of more than 200 h are required in some cases.

EP 1 894 621 A1 describes a gas phase process for preparing isoolefins with an alkali metal- and/or alkaline earth metal-doped silicon-aluminium mixed oxide as a catalyst, which is prepared by treating the commercially available silicon-aluminium mixed oxide prepared by precipitation with an aqueous alkali metal or alkaline earth metal salt solution under acidic conditions with subsequent calcination. The catalyst described is used to achieve, at a conversion of approximately 85%, high isobutene selectivities of >99% and likewise high methanol selectivities of >99%. With increasing experimental duration, the conversion, however, falls under otherwise constant experimental conditions (temperature, pressure, residence time, amount of catalyst, feed composition). In order still to be able to ensure a high conversion, it is necessary to continuously raise the temperature. As a result, however, the mass of secondary components rises and the selectivity for the main components falls. Particularly the formation of dimethyl ether rises.

Cleavage in liquid phase or gas/liquid phase has the disadvantage that the products formed, dissolved in the liquid phase, can more easily enter into side reactions. For example, the isobutene formed in the cleavage of MTBE can form unwanted $C_8$ and $C_{12}$ components as a result of acid-catalysed dimerization or oligomerization. The unwanted $C_8$ components are principally 2,4,4-trimethyl-1-pentene and 2,4,4-trimethyl-2-pentene. In addition, particularly over basic catalysts, a proportion of the methanol formed in the cleavage is converted to dimethyl ether with elimination of water. If the reaction is not performed under pressures above the saturation vapour pressure of the reaction mixture in order to counter these problems, an additional solvent is needed.

In the gas phase, the formation of bi-products as a result of the reaction of the cleavage products with themselves can be suppressed due to the lower concentrations thereof compared to cleavage in the liquid phase. However, other side reactions can occur due to the higher cleavage temperatures. In the gas phase cleavage, there is therefore a requirement for catalysts which, with very high selectivity, catalyse the cleavage of tertiary alkyl ethers or tertiary alcohols to isoolefin and alcohol or water, but do not promote any side reactions, for example C—C cleavage or dehydrogenation, and C—C coupling reactions or ether formation from the alcohols formed. In addition, these catalysts should enable high space-time yields and have a long service life. Furthermore, cleavage of the reactant with maximum selectivity for the isoolefin formed at a pressure of greater than 0.3 MPa (abs) is desirable.

The known catalysts have, in the cleavage of alkyl tert-alkyl ethers or tertiary alcohols to isoolefin and alcohol or water, one or more disadvantages:

a) excessive formation of unwanted by-products, for example dimethyl ether or oligomers of the product olefins.
 b) low service life of the catalyst.
 c) increased formation of by-products when the reaction temperature is raised to compensate for loss of activity.
 d) complex and hence costly preparation of the catalyst.

It was therefore an object of the present invention to provide a cleavage catalyst which does not have one or more of these disadvantages.

It has now been found that, surprisingly, particular silicon- and aluminium-containing mixed oxide powders which have been produced using a silicon-aluminium mixed oxide prepared by flame hydrolysis or pyrogenic means have a high catalytic activity for the cleavage of alkyl tert-alkyl ethers or tertiary alcohols to isoolefin and alcohol or water with simultaneously very low formation of unwanted by-products. It may be advisable in some cases to dope these mixed oxides with alkali metal oxides or alkaline earth metal oxides.

The mixed oxides are prepared in the manner of flame hydrolysis, described inter alia in DE 198 47 161 A1, DE 196 50 500 A1, EP-A 0850 876 and Koth et al., Chem.-Ing.-Tech. 1980, 52, 628ff.

In what is called the "co-fumed process", volatile silicon and aluminium compounds, usually silicon tetrachloride and aluminium trichloride, are injected into an explosive gas flame of hydrogen and oxygen or air. The volatile silicon and aluminium compounds are hydrolysed by the water formed in the explosive gas flame to form the mixed oxide and the acid of the counterion of the silicon and aluminium compounds.

In the doping process used as an alternative, an aerosol is fed into a hydrogen/oxygen gas flame in which an oxide, e.g. silicon oxide, is obtained from a volatile compound, e.g. silicon tetrachloride, by flame hydrolysis, said aerosol containing a salt of the element to be doped, e.g. aluminium, and the corresponding mixed oxide thus being formed.

In both processes, the resulting coproducts are subsequently removed in various steps, as described inter alia in DE 198 47 161 A1, DE 196 50 500 A1, EP-A 0850 876 and Koth et al., Chem.-Ing.-Tech. 1980, 52, 628ff.

The oxides or mixed oxides prepared by flame hydrolysis are notable for the following special features:
 1. high chemical purity,
 2. defined spherical primary particles,
 3. virtually no internal surface area.

In addition, the inventive silicon-aluminium mixed oxide powders are notable in that they are present predominantly or completely in the form of aggregated primary particles and in which a. the weight ratio $(Al_2O_3/SiO_2)_{ttl}$ in the overall primary particle is 0.002 to 0.05, preferably 0.003 to 0.015, more preferably 0.005 to 0.01,
b. the weight ratio $(Al_2O_3/SiO_2)_{surface}$ of the primary particles in a layer close to the surface having a thickness of approx. 5 nm is less than in the overall primary particle and
c. the BET surface area is 50 to 250 m$^2$/g, preferably 100 to 200 m$^2$/g.

The inventive silicon-aluminium mixed oxide powder has the feature, among others, that the proportion of the aluminium oxide relative to the silicon dioxide is very low and the weight ratio $(Al_2O_3/SiO_2)$ surface of the primary particles in a layer close to the surface is lower than in the overall primary particles. This means that the aluminium oxide concentration at the surface is reduced further. The overall primary particle also includes the proportion of silicon dioxide and aluminium oxide in the layer close to the surface. Preference may be given to an inventive silicon-aluminium mixed oxide powder in which $(Al_2O_3/SiO_2)_{ttl}/(Al_2O_3/SiO_2)$ surface is 1.3 to 20, preferably 1.4 to 10 and more preferably 1.6 to 5, where "ttl." represents the overall primary particle.

In a preferred embodiment of the invention, the silicon-aluminium mixed oxide powder has a weight ratio of $(Al_2O_3/SiO_2)_{ttl}$ of 0.005 to 0.015, a ratio $(Al_2O_3/SiO_2)_{ttl}/(Al_2O_3/SiO_2)$ surface of 1.3 to 20 and a BET surface area of 100 to 200 m$^2$/g.

A mixed oxide powder shall be understood to mean an intimate mixture of the mixed oxide components aluminium oxide and silicon dioxide at the atomic level, in which the primary particles also have Si—O—Al bonds. The surfaces of these primary particles are then substantially or completely free of pores.

Preference may be given to those inventive silicon-aluminium mixed oxide powders which are obtained by flame hydrolysis and/or flame oxidation of silicon and aluminium compounds in a flame, produced by the reaction of hydrogen and oxygen. These powders are referred to as "pyrogenic" or "fumed". The reaction at first forms finely divided primary particles which coalesce later in the reaction to aggregates, and these can aggregate further to form agglomerates.

The weight ratio on the surface can be determined, for example, by x-ray-induced photoelectron spectroscopy (XPS analysis) of the powder. Additional information about the surface composition can be determined by energy-dispersive x-radiation (TEM-EDX analysis) of individual primary particles.

The weight ratio in the overall primary particle is determined by chemical or physicochemical methods, for example x-ray fluorescence analysis) of the powder.

It has initially been found that it may be advantageous when the silicon-aluminium mixed oxide powder has a dibutyl phthalate number, in g or dibutyl phthalate (DBP)/100 g of mixed oxide, of 300 to 350. The DBP number is a measure of the structure of aggregates. Low numbers correspond to low structure, high numbers to high structure. The preferred range from 300 to 350 corresponds to high structure. In the case of DBP absorption, the force recorded, i.e. the torque (in Nm), of the rotating paddles of the DBP measuring instrument is measured with addition of defined amounts of DBP, in a comparable manner to a titration. For the inventive powder, a sharp maximum is found with a subsequent decline at a particular addition of DBP. The dibutyl phthalate absorption can be measured, for example, with a RHEOCORD 90 instrument from Haake, Karlsruhe. For this purpose, 12 g of the silicon-aluminium mixed oxide powder is introduced accurately to 0.001 g into a kneading chamber which is closed with a lid, and dibutyl phthalate is metered in through a hole in the lid at a given metering rate of 0.0667 ml/s. The kneader is operated at a motor speed of 125 revolutions per minute. On attainment of the maximum torque, the kneader and the DBP metering are automatically switched off. The amount of DBP consumed and the amount of particles weighed in are used to calculate the DBP absorption according to: DBP number (g/100 g)=(DBP consumption in g/starting weight of powder in g)×100.

The invention further provides a process for producing the inventive silicon-aluminium mixed oxide powder, in which
a) a vapour comprising one or more silicon compounds, selected from the group consisting of $CH_3SiCl_3$, $(CH_3)_2SiCl_2$, $(CH_3)_3SiCl$ and $(n-C_3H_7)SiCl_3$ and the vapour of a hydrolysable and oxidizable aluminium compound are transferred separately or together, by means of a carrier gas, into a mixing chamber, where the weight ratio of aluminium compound, calculated as $Al_2O_3$, to silicon compound, calculated as $SiO_2$, is 0.003 to 0.05,
b) separately therefrom, at least one combustion gas and air are transferred into this mixing chamber, where the total amount of oxygen in the air is at least sufficient for complete combustion of the combustion gas and of the silicon compounds and aluminium compounds,
c) the mixture of the vapour of the silicon compounds and of the aluminium compounds, combustion gas and air is ignited in a burner and the flame burns into a reaction chamber,
d) then the solids are removed from gaseous substances, and the solids are subsequently treated with water vapour.

The process can also be executed in such a way that the vapour of the silicon compounds may contain up to 40% by weight of $SiCl_4$. Particular preference may be given to a mixture of 65 to 80% by weight of $CH_3SiCl_3$ and 20 to 35% by weight of $SiCl_4$. A suitable aluminium compound is preferably aluminium chloride. The combustion gas is preferably selected from the group consisting of hydrogen, methane, ethane, propane and mixtures thereof. Particular preference is given to hydrogen. The air introduced into the mixing chamber is sufficient at least for complete combustion of the combustion gas and of the silicon compounds and aluminium compounds. In general, an excess of air is used. The treatment with water vapour serves the purpose of very substantially removing chloride residues adhering to the particles, such that the powder contains not more than 1% by weight of chloride, preferably not more than 0.2% by weight of chloride.

In addition, the oxides or mixed oxides produced by flame hydrolysis are x-ray-amorphous. An x-ray-amorphous substance is one whose range of long-range order is below the coherence length of the x-radiation used and hence does not generate any interference pattern.

The present invention also provides mixed oxide compositions comprising the silicon-aluminium mixed oxide powders which are produced in accordance with the invention and additionally comprise alkali metal or alkaline earth metal oxides, the inventive mixed oxide powders being treated with an aqueous alkali metal or alkaline earth metal hydroxide solution such that the pH is in the range from 5 to 6.5.

The alkali metals or alkaline earth metals can be introduced in various ways. It can be effected, for example, by impregnating the mixed oxide produced by flame hydrolysis with an alkali metal and/or alkaline earth metal salt solution. Another option is the mixing of the mixed oxide produced by flame hydrolysis with an alkali metal and/or alkaline earth metal salt prior to the actual production of the catalyst.

The invention further provides mixed oxide compositions comprising the silicon-aluminium mixed oxide powders which are produced in accordance with the invention and are additionally treated with an acidic aqueous solution, the pH being in the range from 0 to 6.

It is advantageous when the mixed oxide composition is treated with a phosphorus source, in the production process. The phosphorus source used may be phosphoric acid, phosphonic acid, phosphinic acid, polyphosphoric acid or dihydrogenphosphate, preferably phosphoric acid. The treatment is effected by suspending the mixed oxide composition in water and admixing this suspension with the phosphorus source, such that a pH of 0 to 6, preferably of 1 to 2.5, and especially of 2 to 2.5 is established. Subsequently, the treated catalyst is washed with water, dried at 100 to 150° C. and calcined at 300 to 600° C., preferably at 450 to 550° C.

The proportions by mass of the respective components of the mixed oxide composition may assume the following values:
a) silicon: 50-99.9% by mass (calculated as $SiO_2$),
b) aluminium: 0.1-50% by mass, preferably 0.1-20% by mass, more preferably 1-11% by mass (calculated as $Al_2O_3$),
c) alkali metal: 0-15% by mass (calculated as $M_2O$) or alkaline earth metal: 0-30% by mass (calculated as MO).

A further embodiment of the invention is characterized in that the inventive mixed oxide compositions are used to produce, with addition of binders, temporary assistants and fixatives, shaped bodies in a shaping process.

The present invention likewise provides for the use of the inventive mixed oxide compositions as a catalyst for cleaving a starting compound of the formula II

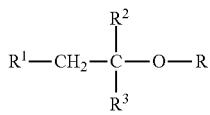

to isoolefins of the formula I

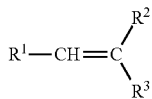

and a compound of the formula III

     III where the R radical in the formulae I to III is H or an alkyl radical having one or two carbon atom(s), the R1 radical is H, or a methyl or ethyl radical and the R2 and R3 radicals are each methyl or ethyl radicals, where the R2 and R3 radicals may be the same or different, at a temperature of 110 to 450° C. and a pressure of 0.1 to 2 MPa(abs).

The present invention likewise provides a process for cleaving a starting compound of the formula II

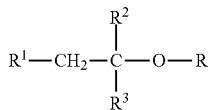

to isoolefins of the formula I

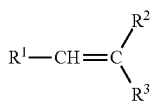

and a compound of the formula III

     III where the R radical in the formulae I to III is H or an alkyl radical having one or two carbon atom(s), the R1 radical is H, or a methyl or ethyl radical and the R2 and R3 radicals are each methyl or ethyl radicals, where the R2 and R3 radicals may be the same or different, at a temperature of 110 to 450° C. and a pressure of 0.1 to 2 MPa(abs), characterized in that the catalyst used is a mixed oxide composition which is produced by flame hydrolysis and in which the proportions by mass of the respective components of the mixed oxide composition may assume the following values:

a) silicon: 50-99.9% by mass (calculated as $SiO_2$),
b) aluminium: 0.1-50% by mass, preferably 0.1-20% by mass, more preferably 1-11% by mass (calculated as $Al_2O_3$),
c) alkali metal: 0-15% by mass (calculated as $M_2O$) or alkaline earth metal: 0-30% by mass (calculated as MO).

In particular embodiments of the invention, alkali metal or alkaline earth metal oxides are additionally present in the mixed oxide composition used as a catalyst for the above-described process, for which purpose the mixed oxide composition is treated with an aqueous alkali metal or alkaline earth metal hydroxide solution such that the pH in the course of treatment is in the range from 5 to 6.5.

A further embodiment of the invention is characterized in that the mixed oxide composition used as a catalyst for the above-described process is treated during preparation thereof with an aqueous acidic solution such that the pH in the course of treatment is in the range from 2 to 2.5.

The preparation of isoolefins by gas phase cleavage of alkyl tert-alkyl ethers (ATAEs) or tertiary alcohols using the inventive mixed oxide composition as a catalyst has several advantages: even in the case of conversions of food stocks exceeding 70%, the corresponding isoolefins form in selectivities exceeding 99%. In the case of cleavage of alkyl tert-butyl ethers (ATBEs), the selectivities for the ethers formed from the alcohol eliminated are below 30%. The cleavage can be performed at relatively low temperatures for cleavage reactions of 110 to 450° C., preferably at temperatures of 180 to 300° C. The conversions can be performed at pressures of greater than 0.3 MPa (abs), such that condensation of the isoolefins formed against cooling water is possible. The catalyst is notable for a long service life. The catalyst does not contain any heavy metals, and so substances of ecological concern occur neither in the course of production thereof nor in the course of disposal thereof. By varying the proportion of alkali metal oxide or alkaline earth metal oxide, the activity can be adjusted optimally for any reactant.

The process according to the invention for preparing the catalyst is notable in that a silicon-aluminium mixed oxide produced by flame hydrolysis is used as a catalyst component.

The inventive mixed oxide composition used as a catalyst may, as well as the elements aluminium, silicon and oxygen, also contain alkali metal and/or alkaline earth metals. For the variant of conducting the reaction in fixed bed reactors, which is of industrial interest, it is necessary that the above-described mixed oxide composition produced by flame hydrolysis or pyrogenic means is subjected, with addition of a binder, to a shaping process, as sufficiently well known in the prior art. The suitable binders used may, as well as aluminas, ceramic clays, colloids, for example, also be amorphous zeolites. Appropriately, the mixed oxide compositions produced by flame hydrolysis and modified in this way are used in a form in which they offer low flow resistance, for example in the form of granules, pellets or shaped bodies, for example tablets, cylinders, spheres, extrudates or rings.

For instance, generally 1-20% by mass of the mixed oxide composition produced by flame hydrolysis is mixed vigorously with a dry binder as specified above, together with temporary assistants, for example water, aqueous solutions, water substitutes, for example glycols, polyglycols, and additionally fixatives, for example cellulose ethers, plasticizers, for example polysaccharides, pressing aids, for example nonionic wax dispersions. This operation can be effected, for example, in a kneader or intensive mixer. Subsequently, a shaping process, for example pelletization, extrusion or dry pressing, produces the shaped bodies for the fixed bed reactor. Prior to the incorporation, the shaped bodies are calcined within a temperature range of 200-700° C., which removes the temporary assistants.

In this regard, a further embodiment of the inventive composition is characterized in that the inert, porous carrier material, for example silicon dioxide, using an additional binder selected from the group comprising:
a) aluminas,
b) ceramic clays,
c) colloids is used to produce mouldings in different three-dimensional shapes selected from the group comprising:
i) spherical,
ii) cylindrical,
iii) ellipsoidal,
iv) polylobular bodies
in a size range of 1-10 mm.

The inventive catalyst preferably has a BET surface area (determined by volumetric means with nitrogen to DIN ISO 9277) of 5 to 600 m$^2$/g, preferably of 20 to 200 m$^2$/g. If the inventive catalyst is applied as an active composition on a support, only the active composition has a BET surface area within the range specified. The pore volume of the inventive catalyst is preferably from 0.5 to 2.0 ml/g, more preferably from 0.8 to 1.5 ml/g. The pore volume is preferably determined by the cyclohexane method. (In this method, the sample to be tested is first dried to constant weight at 110° C. Subsequently, approx. 50 ml of the sample weighed accurately to 0.01 g are introduced into a cleaned impregnation tube which has been dried to constant weight and which has, at the lower end, an outlet orifice with a ground-glass tap. The outlet orifice is covered with a small piece of polyethylene, which prevents blockage of the outlet orifice by the sample. After the impregnation tube has been filled with the sample, the tube is carefully sealed air-tight. Subsequently, the impregnation tube is connected to a water-jet pump, the ground-glass tap is opened and the water jet is used to establish a pressure in the impregnation tube of 20 mbar (absolute). The pressure can be checked on a manometer connected in parallel. After 20 min., the ground-glass tap is closed and the evacuated impregnation tube is subsequently connected to a cyclohexane reservoir in which an accurately measured volume of cyclohexane is initially charged, such that opening of the ground-glass tap results in suction of cyclohexane from the reservoir into the impregnation tube. The ground-glass tap remains open until the entire sample has been flooded with cyclohexane. Subsequently, the ground-glass tap is closed again. After 15 min., the impregnation tube is ventilated cautiously and the unabsorbed cyclohexane is discharged into the reservoir. Cyclohexane adhering in the impregnation tube or in the outlet orifice or the connection with the cyclohexane reservoir can be conveyed into the reservoir via the ventilation line by a single cautious pressure pulse from a suction ball. The volume of the cyclohexane present in the reservoir is noted. The pore volume is calculated from the absorbed volume of cyclohexane, which is determined from the cyclohexane volume in the reservoir before the measurement minus the cyclohexane volume in the reservoir after the measurement, divided by the mass of the sample analysed).

The inventive catalyst can also be applied to a support, for example a metal, polymer or ceramic support, preferably to a support which is inert in relation to the reaction in which the catalyst is to be used. More particularly, the inventive catalyst may be applied to a metal support, for example a metal sheet or a metal mesh. Such supports provided with the inventive catalyst can be used, for example, as internals in reactors or reactive distillation columns. The supports may also be metal, glass or ceramic spheres, or spheres of inorganic oxides. When the inventive catalyst has been applied to an inner support, the mass and composition of the inert support are not taken into account in the determination of the composition of the catalysts.

The inventive catalyst can also be diluted with inert material. This dilution can be accomplished by mixing the finished catalyst with the inert material before or during the introduction of the catalyst in the reactor, or be effected as early as in the course of production of the catalyst.

The inventive catalyst or a catalyst produced by the process according to the invention can be used as a catalyst for numerous reactions. More particularly, the inventive catalyst or a catalyst produced by the process according to the invention can be used in a process for preparing isoolefins of the formula I

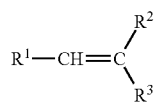

by catalytic gas phase cleavage of a starting compound of the formula II

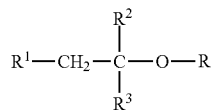

to a compound of the formula I and a compound of the formula III

where the R radical in the formulae I to III is H or an alkyl radical having one or two carbon atom(s), the R$^1$ radical is H, or a methyl or ethyl radical and the R$^2$ and R$^3$ radicals are each methyl or ethyl radicals, where the R$^2$ and R$^3$ radicals may be the same or different, at a temperature of 110 to 450° C. and a pressure of 0.1 to 2 MPa(abs).

The compounds of the formula II used may, for example, be tertiary alcohols having 4 to 6 carbon atoms. Preferably, in such a process according to the invention, tert-butanol (TBA) as compound II is cleaved to isobutene as the compound of the formula I and water as the compound III.

The TBA which is used in the cleavage process according to the invention can originate from various industrial processes. One of the most important is the reaction of isobutenic C$_4$ hydrocarbon mixtures with water. Processes for preparing TBA are disclosed, for example, in patent specifications DE 103 30 710 and U.S. Pat. No. 7,002,050. TBA can be used in pure form, in the form of a TBA/water azeotrope or in the form of another TBA/water mixture.

Preferably, in a cleavage process according to the invention, a compound of the formula II in which R is a methyl or ethyl radical is cleaved. Alkyl tert-alkyl ethers which can be used in the cleavage process according to the invention are, for example, methyl tert-butyl ether, ethyl tert-butyl ether or tert-amyl methyl ether (TAME). More preferably, in the inventive use of the inventive catalyst or of the catalyst produced in accordance with the invention, methyl tert-butyl ether is cleaved to isobutene and methanol, or ethyl tert-butyl ether to isobutene and ethanol.

It is possible in the cleavage process according to the invention to use ATAE which may originate from a wide variety of different processes. A process for preparing MTBE is described, for example, in DE 101 02 062. Processes for preparing ETBE are disclosed, for example, in DE 10 2005 062700, DE 10 2005 062722, DE 10 2005 062699 or DE 10 2006 003492.

The inventive cleavage in the gas phase over the inventive catalyst is preferably performed at a temperature of 110 to 400° C. When the starting material used is MTBE, the cleavage of MTBE to isobutene and methanol is performed preferably at a temperature of 150 to 350° C., more preferably of 180 to 300° C.

The cleavage process according to the invention is preferably performed at a reaction pressure of 0.1 to 2 MPa(abs). When isobutene is a product, it may be advantageous to perform the cleavage process according to the invention at a pressure of 0.2 to 1 MPa(abs), preferably of 0.5 to 0.8 MPa (abs). This is advantageous especially because isobutene can be condensed against cooling water at these pressures.

The specific catalyst space velocity (WHSV; grams of reactant at room temperature per gram of catalyst per hour) in the cleavage process according to the invention is preferably from 0.1 to 100 h$^{-1}$, more preferably from 0.5 to 30 h$^{-1}$. When the starting material used is MTBE, the cleavage of MTBE to isobutene and methanol is performed preferably at WHSV of 0.1 to 100 h$^{-1}$, more preferably of 0.25 to 25 h$^{-1}$.

In order to minimize the complexity of working up the cleavage product mixture, preference is given to aiming for high conversions for the straight pass. Preference is given to performing the process according to the invention in such a way that the conversions of compounds to be cleaved are more than 70%, preferably more than 80% and more preferably more than 90% to 100%. When the reactants comprise troublesome secondary components, it may be appropriate to limit the conversion. When, for example, the feedstock mixture comprises, as well as the MTBE to be cleaved, also 2-methoxybutane, it may be necessary to reduce the conversion in straight pass in order not to exceed a defined ratio of linear butenes to isobutene in the reaction mixture. It may thus be advantageous to limit the permissible conversion of MTBE according to the level of the 2-methoxybutane content in the feedstock mixture comprising MTBE. The limitation of the conversion can be achieved, for example, by increasing the WHSV and/or lowering the reaction temperature.

It may be advantageous for the activity and/or selectivity of some catalysts when proportions of water are added to the reactor feed. For example, JP 19912201 thus describes the continuous addition of water to an alkali metal- or alkali earth metal-doped aluminosilicate to reduce the formation of secondary components.

The optional addition of water for moderation of the catalyst is effected in such a way that the proportion of water in the reactor input is preferably 0 to 5% by mass, more preferably 0.2 to 1.5% by mass. The supply water used is preferably fully demineralized or distilled water or water vapour.

The cleavage product mixture can be worked up by known industrial processes. Unconverted reactant can be recycled into the cleavage, optionally after a partial discharge or purification.

The isoolefins obtained can be utilized as described in the introduction. An isobutene prepared by the cleavage process according to the invention can be used especially for preparation of butyl rubber, polyisobutylene, isobutene oligomers, branched C$_5$-aldehydes, C$_5$-carboxylic acids, C$_5$ alcohols, C$_5$ olefins, tert-butyl aromatics, and methacrylic acid and esters thereof.

The alcohols obtained in the cleavage of ATAE can be reused after workup, for example for synthesis of ATAE.

The process according to the invention and the inventive catalysts are described by way of example hereinafter, without any intention that the invention be restricted to these illustrative embodiments. When ranges, general formulae or compound classes are specified hereinafter, these shall include not only the corresponding ranges or groups of compounds mentioned explicitly, but also all sub-ranges or sub-groups of compounds which can be obtained by selecting individual values (ranges) or compounds.

The examples which follow are intended to illustrate the inventive catalyst and the process using the inventive catalyst.

EXAMPLE 1

Production of the Inventive Silicon-Aluminium Mixed Oxide Powder

The vapour of a mixture consisting of 45 kg/h of CH$_3$SiCl$_3$ and 15 kg/h SiCl$_4$ and the vapour of 0.6 kg/h aluminium chloride are transferred separately from one another, by means of nitrogen as a carrier gas, into a mixing chamber. The vapours are mixed with 14.6 m$^3$ (STP)/h of hydrogen and 129 m$^3$ (STP)/h of dried air in the mixing chamber of a burner and supplied through a central tube, at the end of which the reaction mixture is ignited, and burnt there. The resulting powder is subsequently separated out in a filter and treated with steam at 400-700° C. The powder contains 99% by weight of silicon dioxide and 1% by weight of aluminium oxide. The BET surface area is 173 m$^2$/g. The DBP number is 326 g/100 g of mixed oxide.

To determine the weight ratio $(Al_2O_3/SiO_2)_{surface}$ of the primary particles in a layer close to the surface with a thickness of approx. 5 nm, an XPS analysis is employed. It gives a weight ratio $(Al_2O_3/SiO_2)_{surface}$ of 0.0042. The weight ratio $(Al_2O_3/SiO_2)_{ttl}$ in the overall primary particle is determined by x-ray fluorescence analysis on the powder. It gives a weight ratio $(Al_2O_3/SiO_2)_{ttl}$ of 0.010. This gives rise to a value for $(Al_2O_3/SiO_2)_{ttl}/(Al_2O_3/SiO_2)_{surface}$ of 2.4.

EXAMPLE 2

Production of Catalyst Extrudates (Inventive)

600 g of pyrogenically produced aluminosilicate (1% by mass of Al, calculated as Al$_2$O$_3$), 24 g of a commercial cellulose ether, 21 g of a commercial nonionic wax dispersion as a pressing aid, 3 g of a commercial polysaccharide as a plasticizer, 6 g of 30% aqueous NH$_3$ solution and demineralized water are blended in an intensive mixer with a pin-type agitator. This is followed by pelletization in the intensive mixer, in which homogenously round pellets with a diameter of approx. 1 to 3 mm are obtained within 30-40 minutes. The moist pellets are processed with a commercial extruder to give extrudates of length 3 mm (screw housing 300 mm, screw diameter 80-64 mm, transmission speed 160 rpm, extrusion pressure 31 kg/h). The extrudates thus obtained are dried in an air stream at 120° C. and calcined under air at 600° C.

EXAMPLE 3

Production of Sodium-Doped Catalyst Powder (Inventive)

10 g of pyrogenic aluminosilicate (1% by mass of Al, calculated as Al$_2$O$_3$) and 400 ml of distilled water are transferred into a 500 ml jacketed glass vessel. At the same time, a liebig condenser is present centrally on the reactor in order to prevent the evaporation and escape of liquid phase. The pH of the suspension (approx. 4) is increased by addition of NaOH to the desired value (pH=5, 6, or 6.5). The suspension is stirred with the aid of a magnetic stirrer over the entire reaction time and heated to 70° C. by means of an attached thermostat. After 20 h, the suspension is cooled to ambient temperature and filtered. The solid obtained therefrom is subsequently heated in a muffle furnace at a rate of 1° C./min to 500° C. and calcined at final temperature for 5 h.

EXAMPLE 4

Production of Phosphoric Acid-Treated Catalyst Powder (Inventive)

10 g of pyrogenic aluminosilicate (1% by mass of Al, calculated as $Al_2O_3$) are stirred in 400 ml of distilled water (pH approx. 4). 85% phosphoric acid is added to the suspension until the desired pH is attained (pH=2.5 or pH=2.0). The solution is stirred at room temperature for 2 h, then the solid is filtered off and dried at 120° C. for 1 h (heating rate=1° C./min). Subsequently, the solid obtained therefrom is washed with 500 ml of distilled water, filtered and calcined at 500° C. for 5 h (heating rate=1° C./min).

EXAMPLE 5

Gas Phase Cleavage of Methyl Tert-Butyl Ether (MTBE) to Isobutene and Methanol, and Tert-Butyl Alcohol (TBA) to Isobutene and Water The reactions were conducted in a fully automated catalyst test apparatus equipped with 12 parallel reactors (800×8 mm) under isothermal conditions at T=498 K and P=0.6 MPa(abs). To increase statistical reliability, two samples of each of the catalysts (starting weight: 0.2 g as a powder) were tested in parallel. The catalyst samples were mixed with granulated quartz in a ratio of 1:5 in order to ensure isothermal temperature characteristics in the catalyst bed. The reference catalyst used is an aluminosilicate doped with 10% by mass of magnesium (calculated as MgO) and having an aluminium content of 21% by mass (calculated as $Al_2O_3$), commercially available as Specialyst 071 from Evonik Degussa GmbH.

MTBE is metered in in liquid form via a mass flow regulator and converted to the gas phase in a vapourizer tube (200×24 mm) filled with glass beads (d=2 mm) and connected upstream of the parallel reactors. Downstream of the vapourizer, the gas stream is divided into 12 equal proportions in a divider. This is ensured by downstream restrictors. Each gas stream component is passed through one of the 12 parallel reactors. The offgas leaving the reactors is passed successively through a selection valve to an online gas chromatograph and analysed. The other 11 streams are collected and sent to disposal.

The specific catalyst space velocity (WHSV; grams of reactant per gram of catalyst per hour) was varied between 5 and 50 $h^{-1}$.

TABLE 1

Cleavage of MTBE
Reaction conditions: 225° C., 0.6 MPa(abs), 0.2 g of catalyst; results were obtained onstream at 100 h.

| Catalyst | WHSV [$h^{-1}$] | MTBE conversion [%] | DME selectivity [%] | $C_8$ selectivity [%] |
|---|---|---|---|---|
| A: inventive cat. with 11% by mass of Al | 18 | 85 | 1.16 | 0.03 |
| B: inventive cat. with 1% by mass of Al | 18 | 85 | 0.63 | 0.06 |
| C: cat. not according to invention | 8 | 85 | 2.29 | 0.10 |

TABLE 1-continued

Cleavage of MTBE
Reaction conditions: 225° C., 0.6 MPa(abs), 0.2 g of catalyst; results were obtained onstream at 100 h.

| Catalyst | WHSV [$h^{-1}$] | MTBE conversion [%] | DME selectivity [%] | $C_8$ selectivity [%] |
|---|---|---|---|---|
| D: inventive cat. with 50% by mass of Al | 25 | 85 | 1.49 | 0.17 |
| E: inventive cat. with 0.1% by mass of Al and BET = 20 $m^2/g$ | 8 | 35 | 0.07 | 0.01 |
| F: inventive cat. from example 2 (pH 5) | 17 | 85 | 0.35 | 0.08 |
| G: inventive cat. from example 2 (pH 6) | 16 | 85 | 0.37 | 0.06 |
| H: inventive cat. from example 2 (pH 6.5) | 5 | 85 | 0.49 | 0.05 |
| I: inventive cat. from example 3 (pH 2) | 35 | 85 | 0.13 | 0.09 |
| J: inventive cat. from example 3 (pH 2.5) | 28 | 85 | 0.24 | 0.08 |
| K: inventive cat. from 1% by mass of Al and BET = 80 $m^2/g$ | 8 | 85 | 0.92 | 0.05 |

*Al content in each case calculated as $Al_2O_3$
A: pyrogenic Al/Si 11/BET surface area 200 $m^2/g$
B: pyrogenic Al/Si 1/BET surface area 200 $m^2/g$
C: Specialyst 071 (precipitated aluminosilicate with 21% $Al_2O_3$, doped with 10% MgO), product from Evonik Degussa GmbH
D: pyrogenic Al/Si 50/BET surface area 50 $m^2/g$
E: pyrogenic Al/Si 0.1/BET surface area 20 $m^2/g$
F: pyrogenic Al/Si as B, treated with NaOH according to example 3 (pH 5)
G: pyrogenic Al/Si as B, treated with NaOH according to example 3 (pH 6)
H: pyrogenic Al/Si as B, treated with NaOH according to example 3 (pH 6.5)
I: pyrogenic Al/Si as B, treated with $H_3PO_4$ according to example 4 (pH 2)
J: pyrogenic Al/Si as B, treated with $H_3PO_4$ according to example 4 (pH 2.5)
K: pyrogenic Al/Si, BET surface area 80 $m^2/g$

TABLE 2

Cleavage of TBA
Reaction conditions: 225° C., 0.6 MPa (abs), 0.2 g of catalyst; results were obtained onstream at 100 h.

| Catalyst | WHSV [$h^{-1}$] | TBA conversion [%] | $C_8$ selectivity [%] | $C_{12}$ selectivity [%] |
|---|---|---|---|---|
| Cat. not according to invention (Specialyst 071) | 75 | 80 | 0.11 | 0.05 |
| Cat. according to invention with 1% by mass of Al | 75 | 99 | 0.01 | 0.01 |

*Al content in each case calculated as $Al_2O_3$

EXAMPLE 6

Long-Term Experiment, Gas Phase Cleavage of Methyl Tert-Butyl Ether (MTBE) to Isobutene and Methanol The cleavage was conducted in a fixed bed reactor with a heating jacket, through which a heat carrier oil (Marlotherm S H from Sasol Olefins & Surfactants GmbH) flowed. The reactant used was MTBE of technical grade quality (Diveron from Evonik Oxeno GmbH) with a purity of 99.7% by mass.

Prior to entry into the reactor, the MTBE was fully vapourized in a vapourizer at 180-270° C. At a temperature of 180-270° C. (temperature of the Marlotherm in the feed of the reactor jacket) and a pressure of 0.6 MPa(abs), 1500 g per hour of MTBE were passed through 300 g of catalyst, corresponding to a WHSV of 5 h$^{-1}$. The gaseous product mixture was analysed by gas chromatography. To compensate for the progressive catalyst deactivation, the temperature was increased continuously such that a conversion of 85% was always achieved.

The catalysts used as the inventive catalyst from example 1 in the form of cylindrical extrudates of size 3 mm, and the noninventive commercial catalyst Specialyst 071 from Evonik Degussa GmbH (precipitated aluminosilicate with 21% Al$_2$O$_3$, doped with 10% MgO) in the form of cylindrical tablets of size 3 mm. Due to the high catalytic activity of the inventive catalyst, it is diluted with two times the mass of inert material, for example a commercial α-Al$_2$O$_3$ such as Spheralite 512, in order to be able to establish an equal WHSV.

The composition of reactant and product mixture was used to calculate the isobutene conversions, the selectivities of dimethyl ether formation (DME selectivity=2*number of moles of the DME formed relative to number of moles of MTBE converted) and the selectivities of octene formation (C$_8$ selectivity=2*number of moles of octene formed relative to number of moles of MTBE converted) at various reaction times. These values were compiled in tables 3 and 4 below.

TABLE 3

Conversions, selectivities and temperatures of the cleavage of MTBE with the catalyst prepared in example 1 (diluted with two times the mass of inert material)

| | Experimental duration [h] | | | | | |
|---|---|---|---|---|---|---|
| | 200 | 400 | 600 | 1000 | 1400 | 1600 |
| Temperature [° C.] | 220 | 230 | 240 | 245 | 248 | 248 |
| MTBE conversion [%] | 85 | 85 | 85 | 85 | 85 | 85 |
| DME selectivity [%] | 0.15 | 0.3 | 0.4 | 0.6 | 0.7 | 0.7 |
| C$_8$ selectivity [%] | 0.3 | 0.17 | 0.09 | 0.08 | 0.07 | 0.07 |

TABLE 4

Conversions, selectivities and temperatures of the cleavage of MTBE with the comparative catalyst Specialyst 071

| | Experimental duration [h] | | | | | |
|---|---|---|---|---|---|---|
| | 100 | 250 | 500 | 750 | 1000 | 1500 |
| Temperature [° C.] | 240 | 252 | 258 | 259 | 261 | 262 |
| MTBE conversion [%] | 85 | 85 | 85 | 85 | 85 | 85 |
| DME selectivity [%] | 1.6 | 2.4 | 2.9 | 3.2 | 3.4 | 3.7 |
| C$_8$ selectivity [%] | 0.19 | 0.12 | 0.08 | 0.08 | 0.07 | 0.06 |

Interpretation of the Experimental Results

Table 1 in example 5 shows the experimental results of the MTBE cleavage with the inventive catalysts in powder form compared to the noninventive commercially available catalyst Specialyst 071 (likewise as a powder). In addition, inventive catalysts with different aluminium contents and different BET surface areas—20, 50, 80 and 200 m$^2$/g—were compared.

It is evident that the noninventive catalyst C with a DME selectivity of 2.29% has the highest value of all catalysts tested. The catalytic activity is likewise relatively low, since a low WHSV of 8 h$^{-1}$ has to be established to attain the conversion of 85%. The C$_8$ selectivity is likewise quite high at 0.1%.

In comparison, the inventive catalyst B with aluminium content 1% by mass shows the best results. The conversion of 85% is achieved at a WHSV of only 18 h$^{-1}$. At the same time, the selectivities for DME and C$_8$ are very low at values of 0.63% and 0.06% respectively.

Catalyst E with aluminium content 0.1% by mass and BET surface area of 20 m$^2$/g shows even lower selectivities for the by-products, but results only in a conversion of 35% at a WHSV of 8 h$^{-1}$ due to its low catalytic activity.

The inventive catalyst A with aluminium content 11% by mass likewise exhibits relatively low by-product selectivities and a higher catalytic activity than the noninventive reference catalyst. In the case of the DME selectivity, with a value of 1.16%, it is somewhat poorer than the inventive catalyst B with Al content 1% by mass; in the case of the C$_8$ selectivity, in contrast, it is slightly better at 0.03%.

The catalyst D with an aluminium content of 50% by mass exhibits the highest activity of all catalysts tested, but it also exhibits relatively high by-product selectivities.

The NaOH-doped catalysts F, G and H with aluminium content 1% by mass from example 3 exhibit, depending on the pH established, a slightly lower activity than the corresponding undoped catalyst B. However, they exhibit, in comparative terms, even lower by-product selectivities with regard to DME or C$_8$ formation.

The phosphoric acid-moderated catalysts I or J with aluminium content 1% by mass from example 4 exhibit, depending on the pH established, a higher activity than the corresponding unmoderated catalyst B. At the same time, even lower DME formation is observed, while C$_8$ formation is only slightly increased.

Compared to catalyst B with aluminium content 1% by mass and a BET surface area of 200 m$^2$/g, catalyst K with a BET surface area of only 80 m$^2$/g exhibits a lower catalytic activity. The selectivities for the by-products are at a similar level.

In summary, it can be inferred from these results that the novel inventive catalysts exhibit a higher catalytic activity and lower formation of the unwanted by-products dimethyl ether (DME) and 2,4,4-trimethylpentenes (C$_8$). In addition, it is evident that a low aluminium content in the case of the inventive catalysts, for example catalyst E, leads to lower by-product formation, but also to lower catalytic activity. The same trend is evident in the increase in the sodium content.

Table 2 in example 5 shows the results of the cleavage of tert-butanol (TBA) with the inventive catalyst B having an aluminium content of 1% compared to the noninventive, commercially available catalyst C, Specialyst 071, in each case in powder form. It is evident here that the inventive catalyst exhibits both a higher catalytic activity and lower formation of the unwanted by-products 2,4,4-trimethyl-pentenes (C$_8$) and C$_{12}$ components.

Tables 3 and 4 in example 6 show the results of the long-term experiments in MTBE cleavage with the inventive catalyst B having an aluminium content of 1% by mass and the noninventive catalyst C, Specialyst 071, from a pilot plant. Both catalysts were used here not in the form of powders but in the form of shaped bodies. Due to the high catalytic activity, the inventive catalyst B is diluted with twice the mass of inert material (α-aluminium oxide).

In both experiments, it is evident that, due to the slow deactivation, the temperature has to be raised by 20-30° C. within the first approx. 1500 h. In the case of inventive catalyst B, however, this takes place at a lower temperature level compared to the reference catalyst C, and so the temperature limit of the apparatus is not attained until a later stage.

In most cases, in industrial operation, the catalyst lifetime in the cleavage of alkyl tert-alkyl ethers and tert-alcohols, with the aim of preparation of high-purity isoolefins, however, is restricted not by the activity of the catalyst but by the production of unwanted by-products. From a particular amount of by-products, the industrial plant is no longer capable of removing the by-products to such an extent that the desired product specifications are attained. The inventive catalyst B clearly has the advantage here since it forms a lower level of by-products. More particularly, DME, which is difficult to remove, is formed to a lesser degree.

The invention claimed is:

1. A process, comprising:
cleaving a starting compound of formula II:

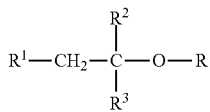  II to isoolefins of formula I:

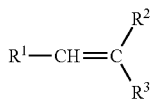  I and a compound of formula III:

  III in the presence of a catalyst,
wherein
R is H or an alkyl radical having one carbon atom or two carbon atoms,
R1 is H, or a methyl or ethyl radical, and
R2 and R3 are each independently a methyl or ethyl radical, and
wherein the catalyst comprises a silicon-aluminium mixed oxide powder, present predominantly or completely as aggregated primary particles, and
an alkali metal or alkaline earth metal oxide,
wherein a weight ratio $(Al_2O_3/SiO_2)_{gt}$ in the primary particles is from 0.002 to 0.05,
a weight ratio $(Al_2O_3/SiO_2)_{surface}$ of the primary particles in a layer close to a surface and having a thickness of approximately 5 nm is less than in the primary particles overall and a BET surface area of the primary particles is from 50 to 250 m$^2$/g.

2. The process according to claim 1, wherein the starting compound is methyl tert-butyl ether.

3. The process according to claim 1, wherein the starting compound is tert-butyl alcohol.

4. The process according to claim 3, wherein the starting compound is tert-butanol in an azeotropic mixture with water.

5. The process according to claim 1, wherein the cleaving is at a temperature of from 110 to 450° C.

6. The process according to claim 1, wherein the cleaving is at a pressure of from 0.1 to 2 MPa(abs).

7. A process, comprising:
cleaving a starting compound of formula II:

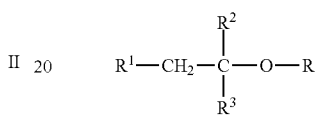  II to isoolefins of formula I:

and a compound of formula III:

  III in the presence of a catalyst,
wherein R is H or an alkyl radical having one carbon atom or two carbon atoms,
R1 is H, or a methyl or ethyl radical, and
R2 and R3 are each independently a methyl or ethyl radical, and
wherein the catalyst comprises:
a silicon-aluminium mixed oxide powder, present predominantly or completely as aggregated primary particles,
wherein a weight ratio $(Al_2O_3/SiO_2)_{nt}$ in the primary particles is from 0.002 to 0.05,
a weight ratio $(Al_2O_3/SiO_2)_{surface}$ of the primary particles in a layer close to a surface and having a thickness of approximately 5 nm is less titan in the primary particles overall,
a BET surface area of the primary particles is from 50 to 250 m$^2$/g, and
the composition is obtained by a process comprising treating with acidic aqueous solution, wherein a pH is within a range from 0 to 6.

* * * * *